United States Patent
Ikushima (10) Patent No.: US 9,877,811 B2
(45) Date of Patent: Jan. 30, 2018

(54) METHOD FOR PRODUCING TEMPORARY PROSTHESIS

(71) Applicant: GC Corporation, Tokyo (JP)

(72) Inventor: Keisuke Ikushima, Tokyo (JP)

(73) Assignee: GC Corporation, Tokyo (JP)

( * ) Notice: Subject to any disclaimer, the term of this patent is extended or adjusted under 35 U.S.C. 154(b) by 444 days.

(21) Appl. No.: 14/426,776

(22) PCT Filed: Sep. 11, 2013

(86) PCT No.: PCT/JP2013/074468
§ 371 (c)(1),
(2) Date: Mar. 9, 2015

(87) PCT Pub. No.: WO2014/045956
PCT Pub. Date: Mar. 27, 2014

(65) Prior Publication Data
US 2015/0245889 A1 Sep. 3, 2015

(30) Foreign Application Priority Data
Sep. 18, 2012 (JP) .................. 2012-203972

(51) Int. Cl.
*A61C 13/107* (2006.01)
*A61C 13/00* (2006.01)
(Continued)

(52) U.S. Cl.
CPC .......... *A61C 13/0001* (2013.01); *A61C 5/70* (2017.02); *A61C 5/73* (2017.02); *A61C 5/77* (2017.02);
(Continued)

(58) Field of Classification Search
CPC .......... A61C 13/0001; A61C 5/70; A61C 5/77; A61C 13/34; A61C 13/20; A61K 6/083; A61K 6/0017
See application file for complete search history.

(56) References Cited

U.S. PATENT DOCUMENTS

| 2,930,124 A | 3/1960 | Pos |
| 4,585,417 A | 4/1986 | Sozio et al. |

(Continued)

FOREIGN PATENT DOCUMENTS

| JP | S53-030957 | 8/1978 |
| JP | H02-034615 | 8/1990 |

(Continued)

OTHER PUBLICATIONS

International Search Report dated Oct. 8, 2013.

*Primary Examiner* — Robert J Grun
(74) *Attorney, Agent, or Firm* — IPUSA, PLLC (57) ABSTRACT

Provided is a method for producing a temporary prosthesis that can be easily performed at a dental clinic and that at the same time enables fabrication of a temporary prosthesis that is less susceptible to wear and damage. The present invention is achieved by fabricating an occlusal surface with a dental composite resin that has higher strength compared to a conventional room temperature polymerization resin. The method includes fabricating a prosthesis model, using an impression material to take an impression of a prepared tooth model having the prosthesis model mounted thereon, applying a layer of dental composite resin material to a portion that is to become a crown within the impression that has been removed from the prepared tooth model and polymerizing the composite resin material, putting a powder-liquid mixture of a powder-liquid type room temperature polymerization resin into the impression, refitting the pre- (Continued)

pared tooth model to the impression, and curing the room temperature polymerization resin.

4 Claims, 12 Drawing Sheets

(51) Int. Cl.
   *A61C 13/34* (2006.01)
   *A61C 5/10* (2006.01)
   *A61C 5/73* (2017.01)
   *A61K 6/00* (2006.01)
   *A61K 6/083* (2006.01)
   *A61C 5/70* (2017.01)
   *A61C 5/77* (2017.01)
   *A61C 13/20* (2006.01)

(52) U.S. Cl.
   CPC ............ *A61C 13/34* (2013.01); *A61K 6/0017* (2013.01); *A61K 6/083* (2013.01); *A61C 13/20* (2013.01)

(56) References Cited

U.S. PATENT DOCUMENTS

| | | |
|---|---|---|
| 5,407,973 A | 4/1995 | Hasegawa et al. |
| 6,660,194 B1 | 12/2003 | Arita |
| 6,852,775 B1 | 2/2005 | Soglowek et al. |
| 2010/0248189 A1 | 9/2010 | Burger et al. |

FOREIGN PATENT DOCUMENTS

| | | |
|---|---|---|
| JP | H05-078531 | 10/1993 |
| JP | H06-219919 | 8/1994 |
| JP | 2001-137263 | 5/2001 |
| JP | 2002-502865 | 1/2002 |
| JP | 2003-502351 | 1/2003 |
| JP | 2004-337419 | 12/2004 |
| JP | 2012-045190 | 3/2012 |
| WO | 99/40884 | 8/1999 |

METHOD FOR PRODUCING TEMPORARY PROSTHESIS

TECHNICAL FIELD

The present invention relates to a method for producing a temporary dental prosthesis to be temporarily inserted until a final definitive prosthesis can be inserted.

BACKGROUND ART

Conventionally, in cases where aesthetics resembling a natural tooth are desired in dental prostheses such as crowns and bridges, resin-faced cast crowns, porcelain-baked-faced cast crowns, resin-faced bridges, porcelain-baked bridges, all-ceramic crowns, and the like may be used, for example. Methods for producing such dental prostheses involve making an impression (counterdie of tooth) from the oral cavity of a patient subjected to formation of an abutment tooth, creating a model (replica of tooth) from the impression using resin or plaster, for example, and fabricating the dental prosthesis based on this model using the lost wax technique, for example. The lost wax technique involves, first preparing a wax pattern of a core portion by applying wax in an abutment tooth die, embedding the wax pattern with a refractory investment material, and after the investment material is hardened, placing the investment material in an electric furnace to burn out the wax pattern. Then, metal is cast into the resulting mold, and after retrieving the cast metal from the investment material, the cast metal is cut and polished to fabricate a metal prosthesis. Alternatively, a dental prosthesis may be fabricated by preparing a metal coping, and thereafter building up and polymerizing hard resin for a crown on the resulting metal coping portion, for example. In the case of fabricating an all-ceramic crown, a composite model is prepared using a refractory die material, and after building up and firing a porcelain material in the composite model, the porcelain material is removed from the composite model and is finished and polished.

Normally, the above procedures are performed by a dental technician, and it generally takes about 3 days to a week before the final prosthesis can be inserted into the mouth of the patient. Meanwhile, in cases where an abutment tooth formed by a dentist is needed, a temporary prosthesis is formed by a dentist, and such a temporary prosthesis is temporarily inserted until the final prosthesis can be inserted. Such a temporary prosthesis is inserted in order to prevent the abutment tooth from being exposed to physical impacts such as food hitting the abutment tooth during a meal, chemical impacts such as exposure to acid, and stimulation from the temperature of food, for example. A temporary prosthesis has other important functions such as maintaining the occlusal function and restoring aesthetics of the teeth, for example.

Conventional temporary prostheses are mainly fabricated using a room temperature polymerization resin (also referred to as "immediate polymerization resin") or a dedicated two-liquid mixture paste resin (see e.g. Patent Documents 1 and 2). The room temperature polymerization resin may be prepared by mixing a (meth)acrylic acid ester polymer powder and a (meth)acrylic acid ester monomer powder solution, for example, and the temporary prosthesis may be fabricated using a mold prepared in advance using the above mixture, for example. Alternatively, the temporary prosthesis may be fabricated directly in the oral cavity of the patient or on a model using the so-called brush-on technique, for example (see e.g. Patent Documents 3 and 4).

However, in general, temporary prostheses fabricated using room temperature polymerization resin or conventional paste resin contain filler at a relatively small ratio and therefore tend to wear easily and have relatively low strength. As such, temporary prostheses have been prone to wear due to occlusion pressure, for example, and cause occlusal problems even when they are used only for a short period of about several days to a week, for example. Also, depending on circumstances such as the schedule of the patient, there may be cases where temporary prostheses are used for up to a few months, and the above problems due to wear become even more conspicuous in such cases. Further, regardless of the use period, conventional temporary prostheses are susceptible to damage or breakage that may be caused by the consumption of tough solid food, for example, and as such, there is a demand for a temporary prosthesis having greater strength.

In recent years, prosthesis fabrication using CAD/CAM technology is becoming widespread, and by using such technology to fabricate a temporary prosthesis, the strength of the temporary prosthesis may be increased (see e.g. Patent Documents 5 and 6). However fabrication procedures using CAD/CAM tend to be more complicated compared to fabrication using room temperature polymerization resin, which can be prepared on site, and the time required for fabrication using CAD/CAM is not much different from fabrication using the lost wax technique.

PRIOR ART DOCUMENTS

Patent Documents

Patent Document 1: PCT Japanese Translation Patent Publication No. 2002-502865
Patent Document 2: PCT Japanese Translation Patent Publication No. 2003-502351
Patent Document 3: Japanese Laid-Open Patent Publication No. H6-219919
Patent Document 4: Japanese Examined Patent Publication No. H5-78531
Patent Document 5: Japanese Laid-Open Patent Publication No. 2001-137263
Patent Document 6: Japanese Laid-Open Patent Publication No. 2012-045190

SUMMARY OF THE INVENTION

Problem to be Solved by the Invention

In view of the above, an object of the present invention relates to providing a method for producing a temporary prosthesis that can be easily performed at a dental clinic and at the same time enables fabrication of a temporary prosthesis that is less susceptible to wear and damage.

Means for Solving the Problem

The present inventor has conceived the present invention by discovering, through diligent research and analysis, that the above problems of the related art can be solved by producing the occlusal surface using a dental composite resin having a higher strength compared to the conventional room temperature polymerization resin.

According to one embodiment of the present invention, a method for producing a temporary prosthesis includes the steps of fabricating a prepared tooth model replicating an oral cavity including a prepared tooth arranged into a shape for receiving the temporary prosthesis, fabricating a prosthesis model having a shape that is identical to a shape of the temporary prosthesis to be formed on the prepared tooth model, using an impression material to take an impression of the prepared tooth model having the prosthesis model mounted thereon, applying a layer of dental composite resin material to a portion that is to become a crown within the impression that has been removed from the prepared tooth model and polymerizing the dental composite resin material, putting a powder-liquid mixture of a powder-liquid type room temperature polymerization resin into the impression, refitting the prepared tooth model to the impression, and curing the room temperature polymerization resin.

According to another embodiment of the present invention, a method for producing a temporary prosthesis includes the steps of fabricating a model replicating an oral cavity including a tooth that is to receive the temporary prosthesis based on an impression of the oral cavity including the tooth, fabricating a prepared tooth model replicating an oral cavity including a prepared tooth arranged into a shape for receiving the temporary prosthesis, applying a layer of dental composite resin material to a portion that is to become a crown within the impression that has been removed from the prepared tooth model and polymerizing the dental composite resin material, putting a powder-liquid mixture of a powder-liquid type room temperature polymerization resin into the impression, fitting the prepared tooth model to the impression, and curing the room temperature polymerization resin.

In one preferred embodiment of the present invention, the dental composite resin material includes a (meth)acrylate compound, a photopolymerization initiator, and a filler; and a ratio of the filler is 45 wt % to 80 wt % of the dental composite resin material.

In another preferred embodiment of the present invention, the powder-liquid mixture of the room temperature polymerization resin includes a liquid component containing a (meth)acrylate compound and a room temperature polymerization initiator, and a powder component containing a poly((meth)acrylate) powder and a room temperature polymerization initiator; and a ratio of a filler mixed into the powder component is less than or equal to 10 wt %.

In another preferred embodiment of the present invention, the dental composite resin material is a photopolymerization type composite resin material.

Advantageous Effect of the Invention

A method for producing a temporary prosthesis according to the present invention can be easily performed at a dental clinic and at the same time enables fabrication of a temporary prosthesis that is less susceptible to wear and damage.

EMBODIMENTS FOR IMPLEMENTING THE INVENTION

Figure 1:
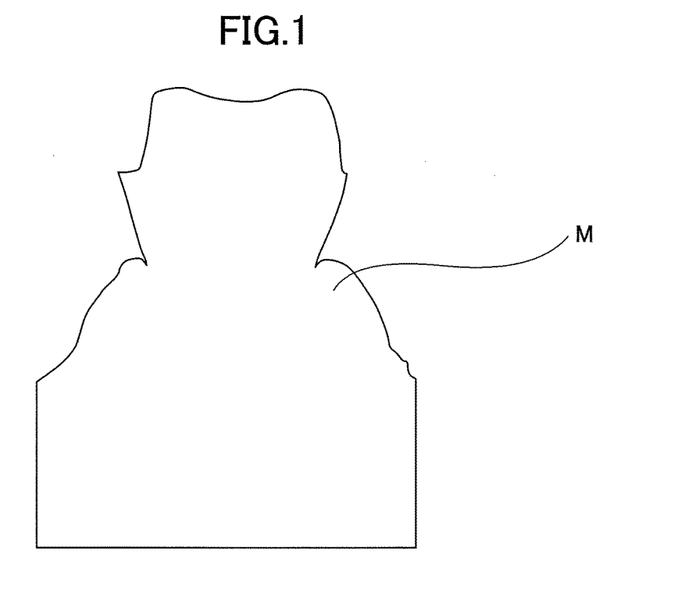
FIG. 1 is a schematic cross-sectional view of section A-A' of a prepared tooth model M replicating an oral cavity including a tooth that is arranged into a shape for receiving a temporary prosthesis.
Figure 15:
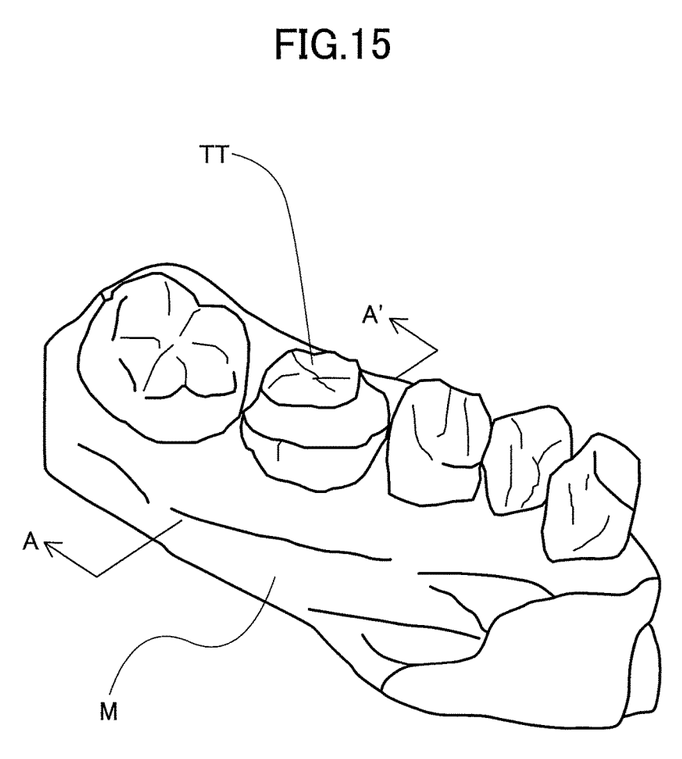
FIG. 15 illustrates the prepared tooth model M replicating the oral cavity including the tooth that is arranged into a shape for receiving the temporary prosthesis.

In the following, methods for producing a temporary prosthesis according to the present invention are described in detail with reference to the accompanying drawings. A first method for producing a temporary prosthesis according to the present invention is described below. First, as illustrated in FIGS. 1 and 15, a prepared tooth model M replicating an oral cavity including a prepared tooth TT that has been arranged into a shape for receiving a temporary prosthesis, namely, a tooth that has been subjected to an abutment tooth or formation of a cavity, is fabricated using a conventional technique. The prepared tooth model M is preferably fabricated using conventional dental plaster but may also be fabricated using other techniques such as polymerization of resin, cutting, 3D printing, and the like, for example.

Figure 2:
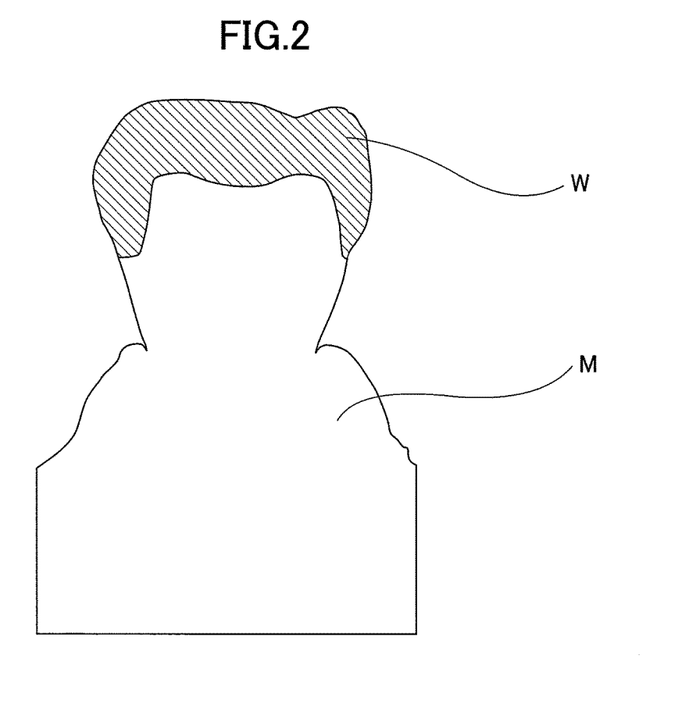
FIG. 2 schematically illustrates a state in which a prosthesis model W is attached to the model of FIG. 1.
Figure 3:
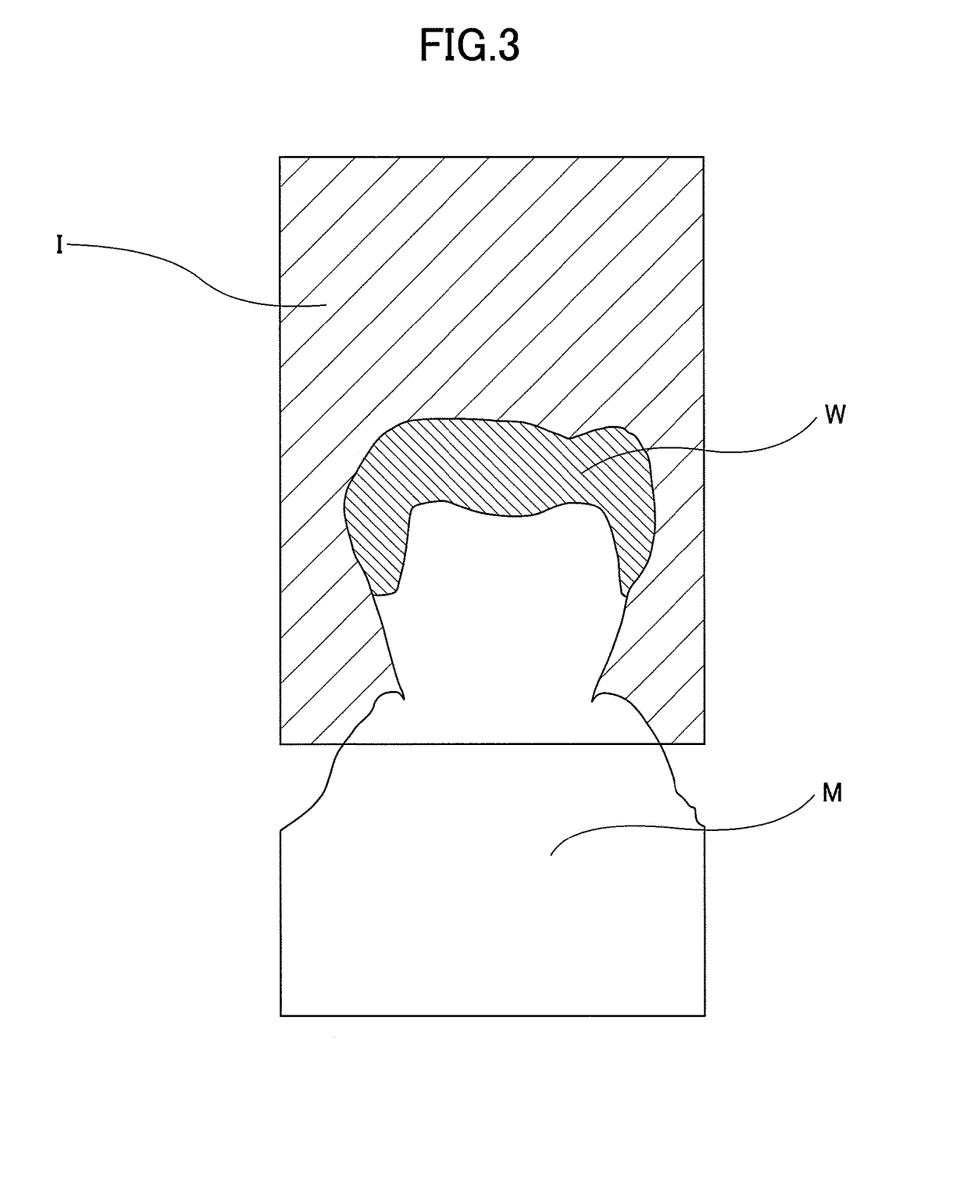
FIG. 3 schematically illustrates a state taking an impression of the model of FIG. 2.

Then, using the prepared tooth model M, a prosthesis model W having the same shape as that of the temporary prosthesis to be produced is fabricated with wax, synthetic resin, and the like (FIG. 2). Then, using a dental impression material, an impression I is taken from the prepared tooth model M having the prosthesis model W mounted thereon (FIG. 3).

Figure 4:
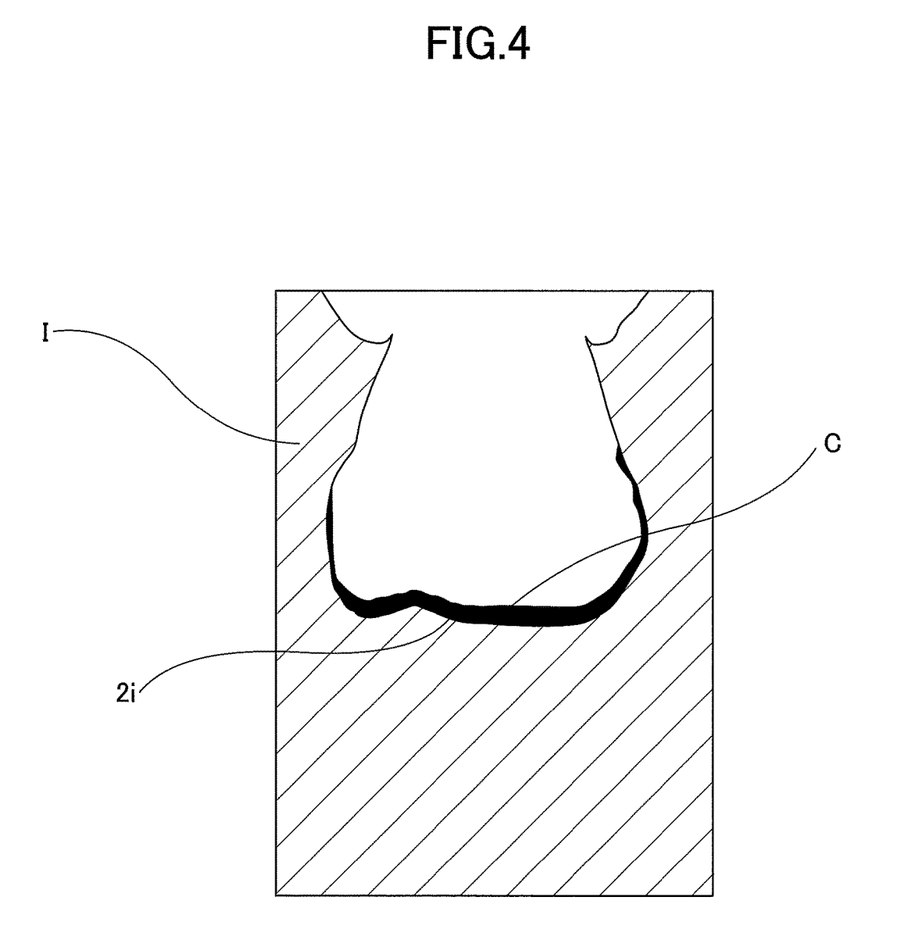
FIG. 4 schematically illustrates a state in which the impression that has been removed from the prepared tooth model and a layer of dental composite resin material has been applied to a portion that is to become a crown within the impression.

Then, the impression I is removed from the prepared tooth model M, a layer of a dental composite resin material C is applied to a portion 2i that is to become a temporary prosthetic crown to be produced within the impression I, and the dental composite resin material C is polymerized (FIG. 4). Note that the dental composite resin material C is intended to be applied to a portion corresponding to where the enamel of a natural tooth is located. As such, normally, a bottom portion of a concave part of the impression I corresponds to the portion 2i that is to become the crown, and the dental composite resin material C is applied to this portion 2i.

Figure 5:
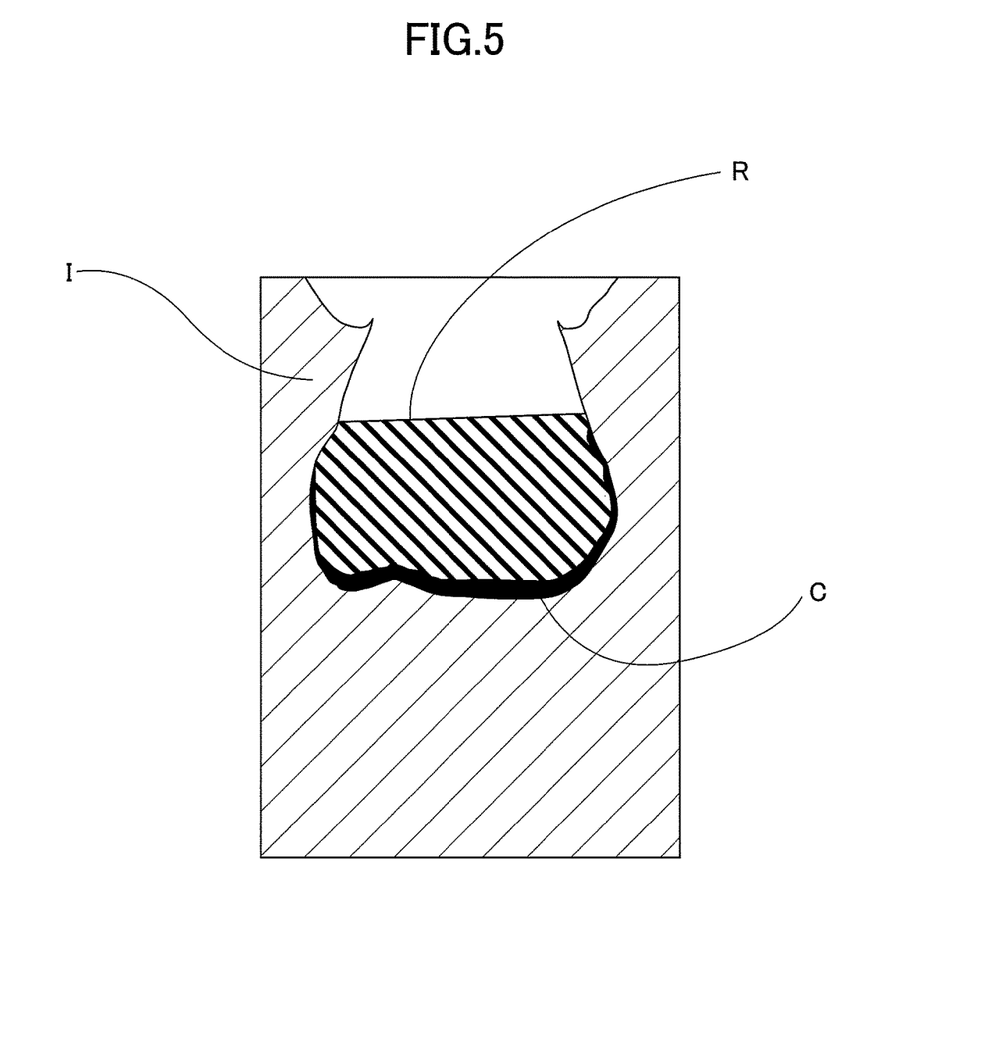
FIG. 5 schematically illustrates a state in which a powder-liquid mixture of a room temperature polymerization resin is filled into the impression of FIG. 4.
Figure 6:
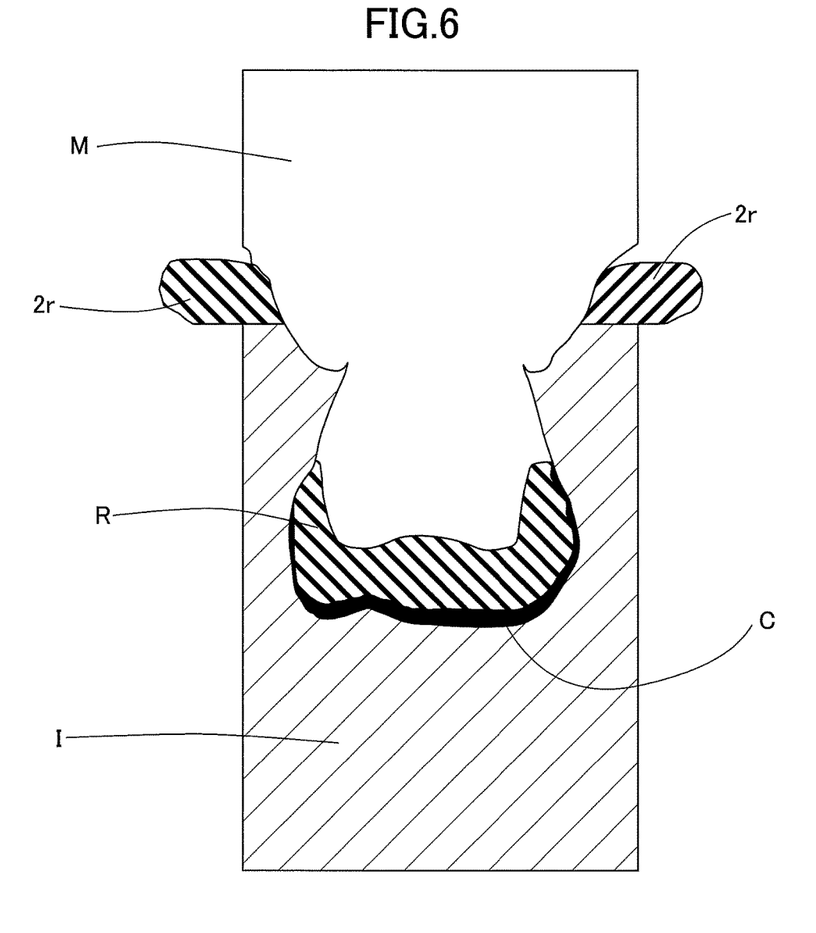
FIG. 6 schematically illustrates a state in which the prepared tooth model is refitted to the impression of FIG. 5.
Figure 7:
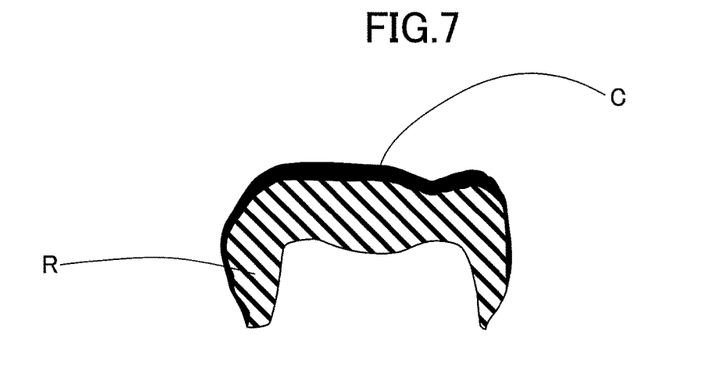
FIG. 7 is a schematic cross-sectional view of a temporary prosthesis that has been fabricated by curing the room temperature polymerization resin, removing the set resin from the impression, and performing adjustments such as finishing and polishing.

Then, a mixture of powder material and liquid material making up a powder-liquid type room temperature polymerization resin R is poured or filled into the impression I (FIG. 5), and the prepared tooth model M having the prosthesis model W removed therefrom is refitted to the impression I (FIG. 6). Note that at this time, excessive room temperature polymerization resin 2r may protrude out from between the prepared tooth model M and the impression I, and this may be removed as necessary. In this state, the room temperature polymerization resin R is cured, removed from the impression I, and adjusted through finishing and polishing, for example, to produce a temporary prosthesis (FIG. 7).

Figure 8:
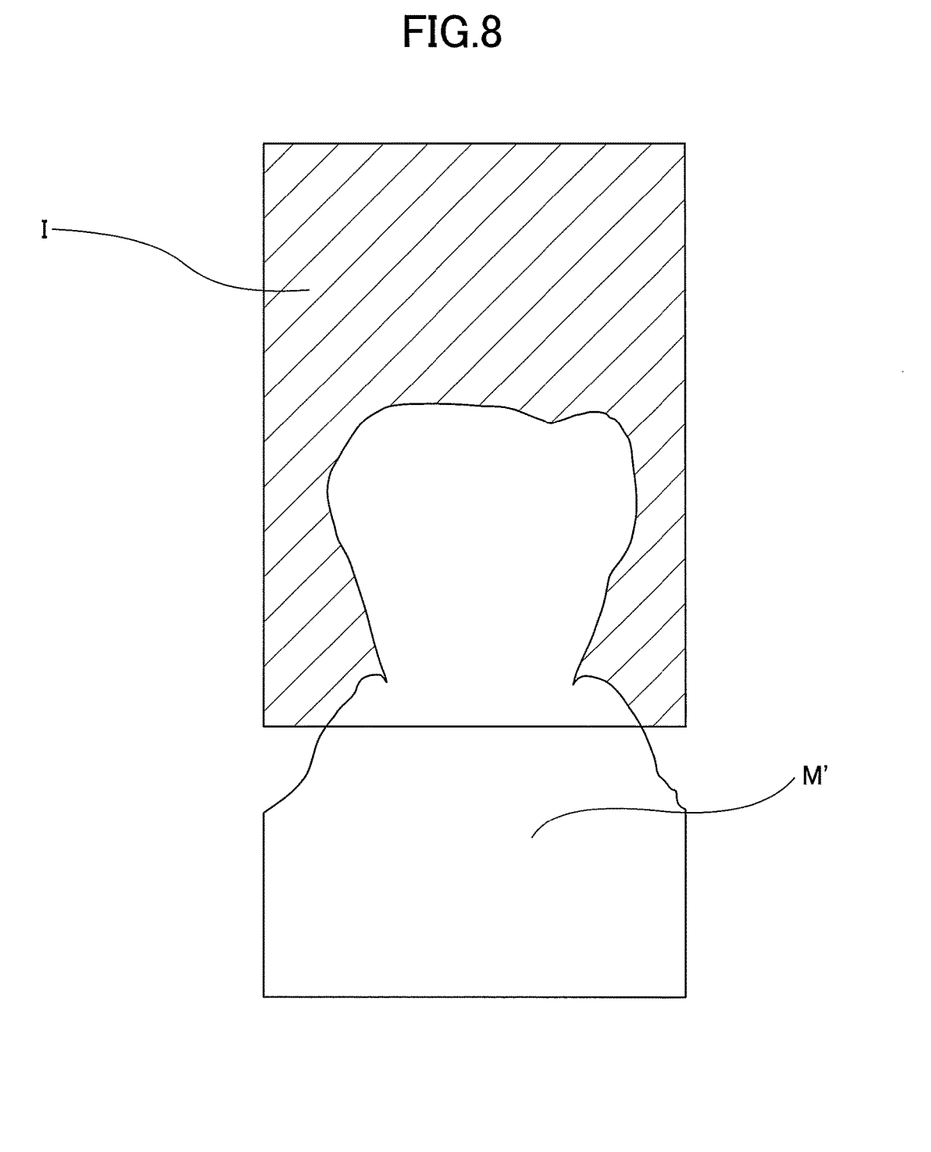
FIG. 8 is a schematic cross-sectional view of section B-B' of an impression of an oral cavity including a tooth that is to receive a temporary prosthesis and a model M' that is fabricated based on the impression.
Figure 9:
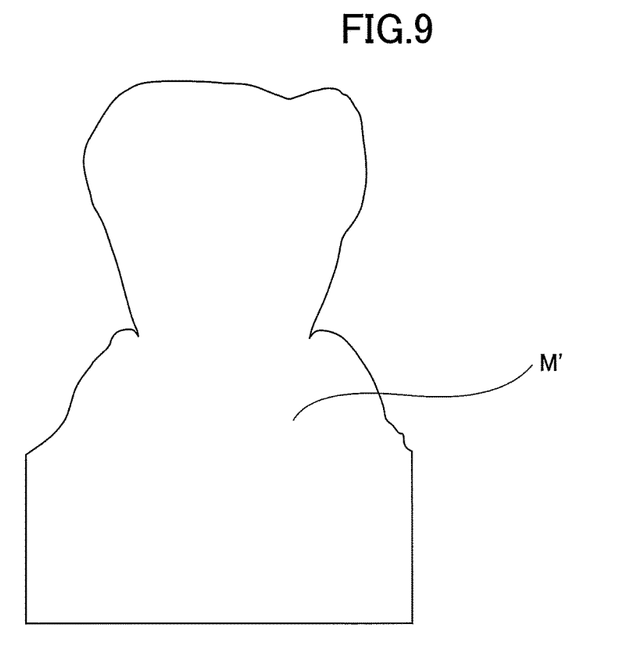
FIG. 9 is a schematic cross-sectional view of section B-B' of the model M' replicating the oral cavity including the tooth that is to receive the temporary prosthesis.
Figure 16:
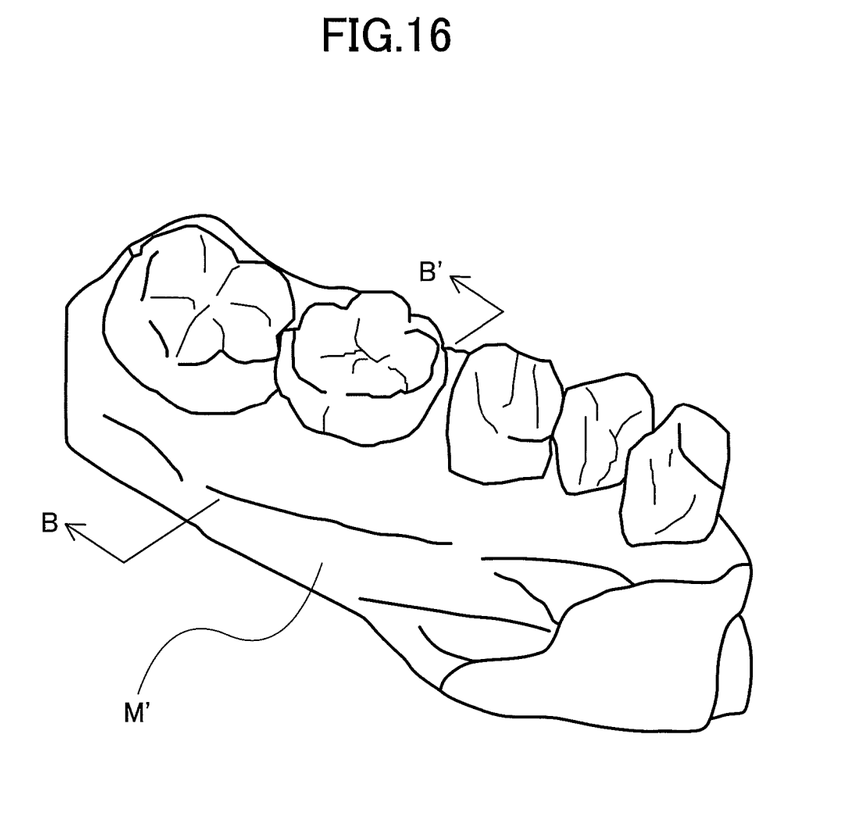
FIG. 16 illustrates the prepared tooth model M' replicating the oral cavity including the tooth that is to receive the temporary prosthesis.

In the following, a second method for producing a temporary prosthesis according to the present invention is described. First, using a conventional technique, a model M' replicating an oral cavity is fabricated (FIGS. 9 and 16) based on an impression I of the oral cavity including a tooth to receive a temporary prosthesis (FIG. 8). The model M' is preferably fabricated using conventional dental plaster but may also be fabricated using other techniques such as polymerization of resin, cutting, 3D printing, and the like, for example.

Figure 10:
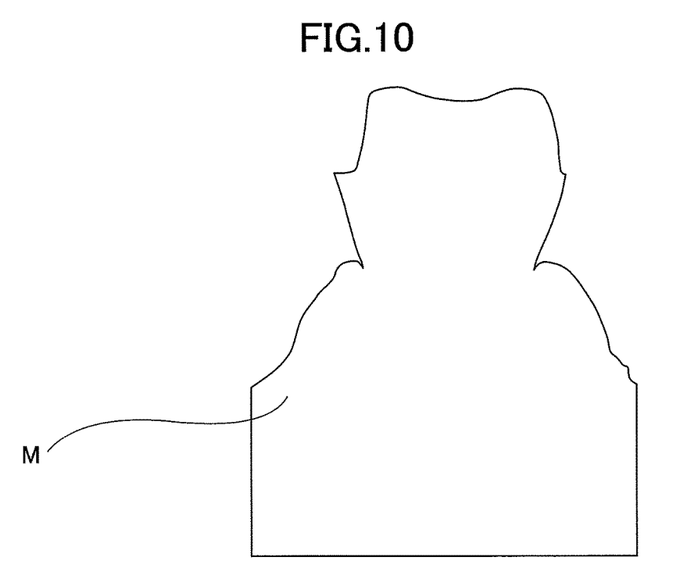
FIG. 10 is a schematic cross-sectional view of section A-A' of the prepared tooth model M replicating an oral cavity including a tooth that arranged into a shape for receiving the temporary prosthesis.
Figure 11:
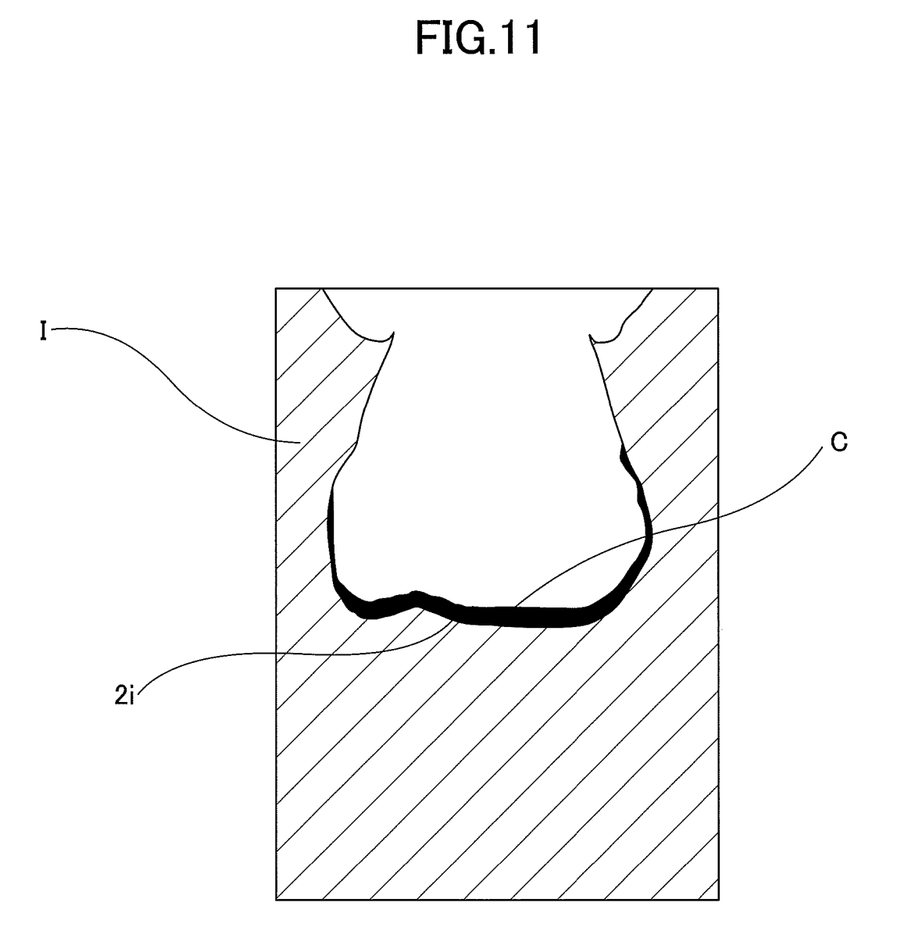
FIG. 11 schematically illustrates a state in which the impression is removed from the model and a layer of dental composite resin material is applied to a portion that is to become a crown within the impression.
Figure 12:
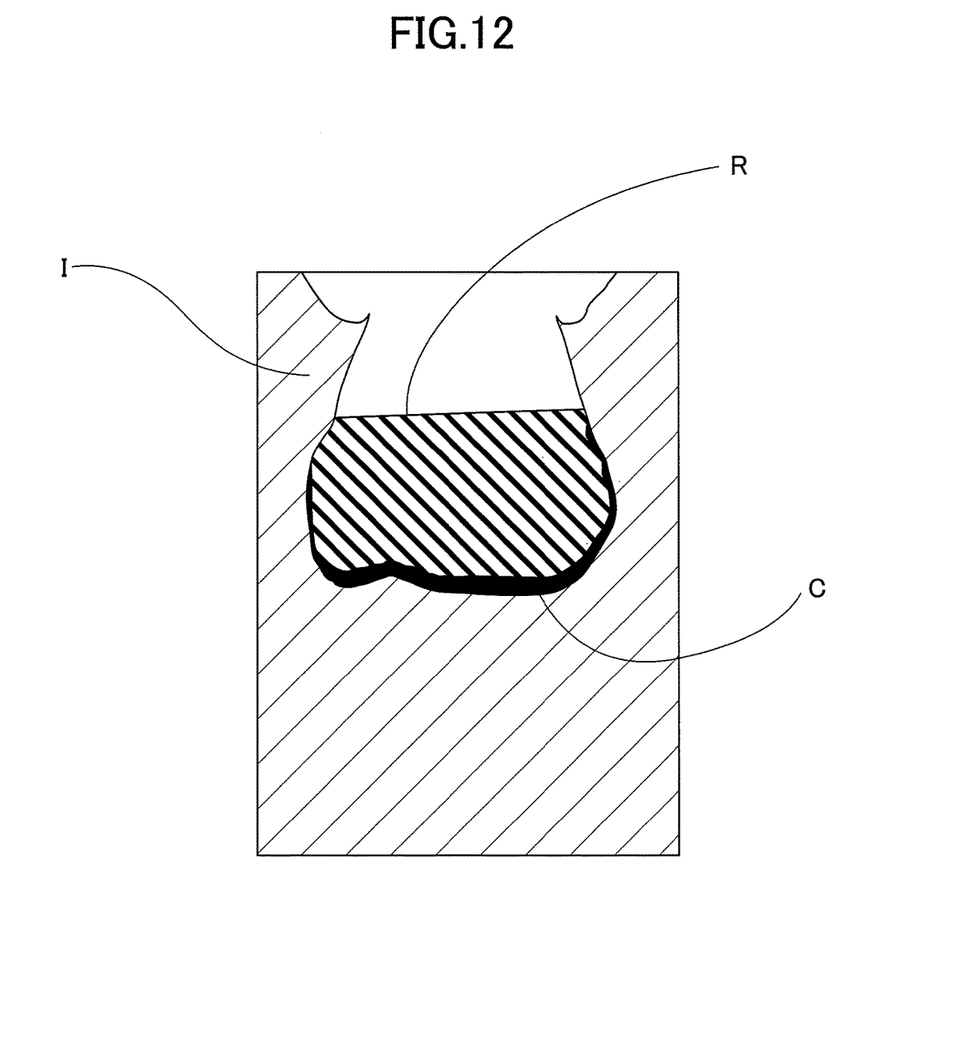
FIG. 12 schematically illustrates a state in which a powder-liquid mixture of a room temperature polymerization resin is filled into the impression of FIG. 11.
Figure 13:
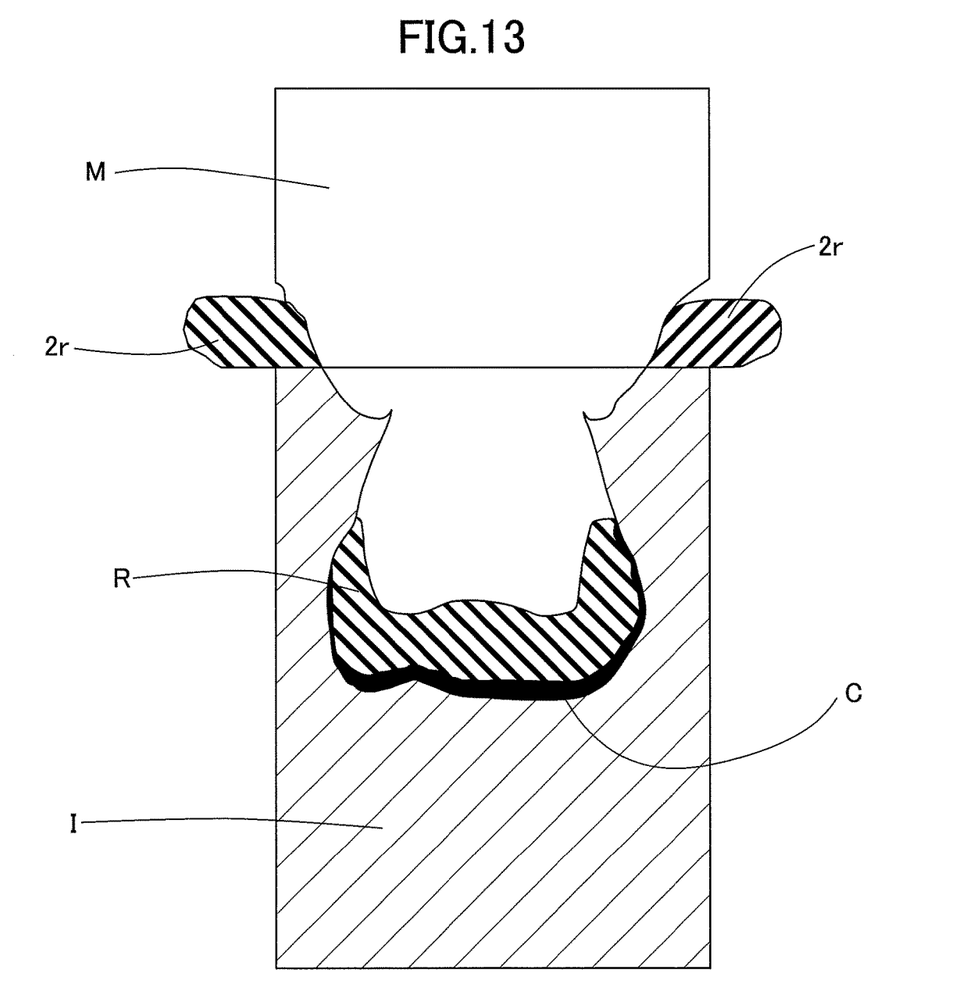
FIG. 13 schematically illustrates a state in which the prepared tooth model is fitted to the impression of FIG. 12.

Then, using a conventional technique, the prepared tooth model M replicating the oral cavity including the prepared tooth TT arranged into a shape for receiving the temporary prosthesis is fabricated (FIGS. 10 and 15). Then, a layer of the dental composite resin material C is applied to a portion 2i that is to become a temporary prosthetic crown to be produced within the impression I, and the dental composite resin material C is polymerized (FIG. 11). Note that the dental composite resin material C is intended to be applied to a portion corresponding to where the enamel of a natural tooth is located. As such, normally, a bottom portion of a concave part of the impression I corresponds to the portion 2ithat is to become the crown, and the dental composite resin material C is applied to this portion 2i. Then, a mixture of powder material and liquid material making up a powder-liquid type room temperature polymerization resin R is poured or filled into the impression I (FIG. 12), and the prepared tooth model M is fitted to the impression I (FIG. 13).

Figure 14:
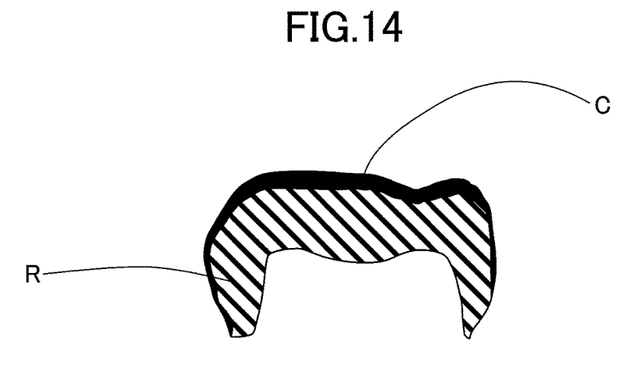
FIG. 14 is a schematic cross-sectional view of a temporary prosthesis that has been fabricated by curing the room temperature polymerization resin, removing the set resin from the impression, and performing adjustments such as finishing and polishing (identical to FIG. 7)

Note that at this time, excessive room temperature polymerization resin 2r may protrude out from between the prepared tooth model M and the impression I, and this may be removed as necessary. In this state, the room temperature polymerization resin R is cured, removed from the impression I, and adjusted through finishing and polishing, for example, to produce a temporary prosthesis (FIG. 14).

In both the first method and the second method for producing a temporary prosthesis according to the present invention, the dental composite resin material C is preferably made of a (meth)acrylate compound, a photopolymerization initiator, and a filler; and the ratio of the filler is preferably 45 wt % to 80 wt % of the composite resin material C. In this way, a temporary prosthesis that is less susceptible to wear and damage may be fabricated as compared with the case of using dental room temperature polymerization resin R.

Examples of the (meth)acrylate compound contained in the composite resin material C used in the method for producing a temporary prosthesis according to the present invention include monomers, oligomers, and prepolymers of methacrylates or acrylates, which are known substances for use as dental materials. Specific examples of the (meth)acrylate compound include methyl (meth)acrylate, ethyl (meth)acrylate, isopropyl (meth)acrylate, n-butyl (meth)acrylate, isobutyl (meth)acrylate, hydro xypropyl (meth)acrylate, tetrahydrofurfuryl (meth)acrylate, glycidyl (meth)acrylate, 2-hydroxyethyl(meth)acrylate, 2-hydroxypropyl (meth)acrylate, 3-hydroxypropyl (meth)acrylate, 2-ethoxyethyl (meth)acrylate, 2-methoxyethyl (meth)acrylate, 2-ethylhexyl (meth)acrylate, benzyl (meth)acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylol(meth)ane tri(meth)acrylate, pentaerythritol tetra(meth)acrylate, polybutylene glycol di(meth)acrylate, bisphenol A polyethoxy (meth)acrylate, bisphenol A diglycidyl(meth)acrylate, and the like. Also other examples include (meth)acrylates having urethane bonds such as di-2-(meth)acryloxyethyl-2,2,4-trimethylhexamethylene dicarbamate, and 1,3,5-tris[1,3-bis((meth)acryloyloxy)-2-(propoxycarbonylamino)hexane]-1,3,5-(1H,3H,5H)triazine-2,4,6-trione; a (meth)acrylate of a urethane oligomer consisting of 2,2'-di(4-hydroxycyclohexyl)propane, 2-oxepanone, hexamethylene diisocyanate, and 2-hydroxyethyl(meth)acrylate; and a (meth)acrylate of a urethane oligomer consisting of 1,3-butanediol, hexamethylene diisocyanate, and 2-hydroxyethyl (meth)acrylate.

The polymerization initiator contained in the composite resin material C used in the method for producing a temporary prosthesis according to the present invention may be used the same as that used in the room temperature polymerization resin R, which is described below. In this case, the composite resin material C has to be divided into two or more components. However, the polymerization initiator of the composite resin material C is preferably a photopolymerization initiator. In this case, the composite resin material C may be used alone. Note that a combination of a sensitizer and a reducing agent is generally used as the photopolymerization initiator. Examples of sensitizers include camphorquinone, benzyl, diacetyl, benzyl dimethyl ketal, benzyl diethyl ketal, benzyl di(2-methoxyethyl)ketal, 4,4'-dimethyl-benzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitro-thioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone 10-oxide, benzoin methyl ether, benzoin ethyl ether, isopropyl ether, benzoin isobutyl ether, benzophenone, bis(4-dimethylaminophenyl)ketone, 4,4'-bisdiethylaminobenzophenone, compounds containing an azide group, and the like. Note that these substances may be used alone or in combination.

Tertiary amine is generally used as the reducing agent. Preferred examples of tertiary amines include dimethylaminoethyl (meth)acrylate, triethanolamine, methyl 4-dimethylaminobenzoate, ethyl 4-dimethylaminobenzoate, and isoamyl 4-dimethylaminobenzoate. Other examples of reducing agents include benzoyl peroxide, organic metal compounds, sulfinic acid derivatives, and the like. Note that a polymerization reaction of the composite resin material C including the above substances may be achieved through irradiation of active light such as ultraviolet or visible light, for example.

As a light source, various types of mercury lamps including an ultra-high pressure type mercury lamp, a high pressure type mercury lamp, a medium pressure type mercury lamp, and a low pressure type mercury lamp; a chemical lamp; a carbon arc lamp; a metal halide lamp; a fluorescent lamp; a tungsten lamp; a xenon lamp; and an argon ion laser may be used, for example. Also, small amounts of an ultraviolet absorber, a coloring agent, a polymerization inhibitor, and the like may be used as necessary.

The filler contained in the composite resin material C used in the method for producing a temporary prosthesis according to the present invention may be any type of filler including organic, inorganic, and composites of organic and inorganic fillers. Examples of substances that may be used include quartz powder, alumina powder, glass powder, kaolin, talc, calcium carbonate, barium aluminosilicate glass, titanium oxide, borosilicate glass, colloidal silica powder, and the so-called organic composite filler that is produced by polymerizing colloidal silica with polymer and pulverizing the same. Examples of polymer powders include poly(methyl (meth)acrylate),methyl(meth)acrylate-co-ethyl (meth)acrylate copolymer, cross-linked polymethyl (meth)acrylate, and ethylene-vinyl acetate copolymer, and the like. In some examples, the above polymer powders may be mixed with the above inorganic powders to be used as the filler.

The ratio of the filler is preferably 45 wt % to 80 wt % with respect to the total weight of the composite resin material C. When the ratio is less than 45 wt %, sufficient strength may not be secured, and when the ratio is greater than 80 wt %, manipulability may be compromised, for example.

Before mixing the filler with the (meth)acrylate compound, the above inorganic filler is preferably treated using a coupling agent that is capable of reacting with both the filler and the (meth)acrylate compound. Examples of the coupling agent that may be used include a silane coupling agent, a titanate coupling agent, an aluminate coupling agent, and the like. Alternatively, the surface of the inorganic filler may be grafted to prompt bonding with a binder resin, for example.

Specific examples of silane coupling agents include γ-methacryloxypropyltrimethoxysilane, vinyl trichlorosilane, vinyl-tris(β-methoxyethoxy)silane, γ-methacryloxypropyl methyl dimethoxysilane, γ-glycidoxypropyltrimethoxysilane, γ-chloropropyl trimethoxysilane, β-(3,4-epoxy cyclohexyl)ethyl trimethoxysilane, trimethylchlorosilane, dimethyldichlorosilane, hexamethyldisilane, γ-aminopropyltriethoxysilane, N-β-(aminoethoxy)-γ-aminopropyltrimethoxysilane, γ-ureido propyl trimethoxysilane, and the like.

In both the first method and the second method for producing a temporary prosthesis according to the present invention, the powder-liquid mixture of the room temperature polymerization resin R preferably includes a liquid component containing a (meth)acrylate compound and a room temperature polymerization initiator, and a powder component containing a poly((meth)acrylate) powder and a room temperature polymerization initiator. The ratio of the filler to be mixed into the powder component is preferably less than or equal to 10 wt %. In this way, a temporary prosthesis may be fabricated at a lower cost as compared with the case of fabricating the entire temporary prosthesis with the dental composite resin material C.

The (meth)acrylate compound and the poly((meth)acrylate) powder contained in the room temperature polymerization resin R that is used in the method for producing a temporary prosthesis according to the present invention may be used the same substances as those used in the above-described composite resin material C. Particularly, liquids and polymer powders of methyl(meth)acrylate and ethyl (meth)acrylate are preferred in terms of reaction speed and hardness after curing.

The room temperature polymerization initiator contained in the room temperature polymerization resin R used in the method for producing a temporary prosthesis according to the present invention may be a combination of an organic peroxide and an aromatic tertiary amine, for example. In the case of using such catalysts, the organic peroxide and the aromatic tertiary amine are separately incorporated into the liquid component and the powder component of the room temperature polymerization resin R, and the components are mixed when the room temperature polymerization resin R is to be used. Preferred examples of organic peroxides that may be used include diacyl peroxides including an aromatic group and peroxy esters that are considered esters of perbenzoic acid. Specific examples include benzoyl peroxide, 2,4-dichloro benzoyl peroxide, m-tolyl peroxide, t-butyl peroxy benzoate, di-t-butyl peroxy isophthalate, 2,5-dimethyl-2,5-di(benzoyl peroxy)hexane, and the like. These substances are typically contained in the powder component.

Preferred examples of tertiary amines that may be used include tertiary amines having an aromatic group directly replaced by a nitrogen atom. Specific examples include N,N-dimethyl-p-toluidine, N,N-dimethylaminoethyl methacrylate, N,N-dimethylaniline, N-methyl-N-β-hydroxy aniline, N,N-di(β-hydroxyethyl)-aniline, N,N-di(β-hydroxyethyl)-p-toluidine, N,N-di(β-hydroxy propyl)-aniline, N,N-di(β-hydroxypropyl)-p-toluidine, triethanolamine, ethyl 4-dimethylaminobenzoate, methyl N,N-dimethylaminobenzoate, ethyl N,N-dimethylaminobenzoate, isoamyl N,N-dimethylaminobenzoate, and the like. These substances are typically contained in the liquid component.

In addition to the above substances, the following substances may also be used as the room temperature polymerization initiator. For example, a combination of a pyrimidinetrione derivative, an organometallic compound, and an organic halogen compound may be used. In this case, the pyrimidinetrione. derivative and the organometallic compound may be mixed into one component of the room temperature polymerization resin R, and the organic halogen compound may be mixed into the other component. Preferred examples of pyrimidinetrione derivatives that may be used include 1-cyclohexyl-5-ethyl pyrimidinetrione, 1-benzyl-5-phenyl pyrimidinetrione, 5-butyl pyrimidinetrione, 5-phenyl pyrimidinetrione, 1,3-dimethyl pyrimidinetrione, 5-ethyl-pyrimidine trione, and the like. These substances are typically contained in the powder component.

Preferred examples of organic metal compounds that may be used include acetylacetone copper, copper 4-cyclohexyl butyric acid, cupric acetate, copper oleate, acetylacetone manganese, manganese naphthenate, manganese octylate, acetylacetone cobalt, cobalt naphthenate, acetylacetone lithium, lithium acetate, zinc acetylacetonate, zinc naphthenate, acetylacetone nickel, nickel acetate, acetylacetone aluminum, calcium acetylacetonate, acetylacetone chromium, acetylacetone iron, sodium naphthenate, rare earth octoates, and the like. These substances are typically contained in the powder component.

Preferred examples of organic halogen compounds that may be used include dilauryl dimethyl ammonium chloride, lauryl dimethyl ammonium chloride, tetra-n-butyl ammonium chloride, trioctylmethylammonium chloride, benzyl dimethyl cetyl ammonium chloride, benzyl dimethyl stearyl ammonium chloride, and the like. These substances are typically contained in the liquid component.

Note that the ratio of the filler contained in the powder component of the room temperature polymerization resin R is preferably less than or equal to 10 wt %. When the ratio is greater than 10 wt %, manufacturing costs tend to increase.

DESCRIPTION OF THE REFERENCE NUMERALS

M prepared tooth model
M' model
I impression
2i portion that is to become a crown
W prosthesis model
C composite resin material
R room temperature polymerization resin
2r excessive room temperature polymerization resin

The invention claimed is:

1. A method for producing a temporary prosthesis, the method comprising the steps of:
    fabricating a prepared tooth model (M) replicating an oral cavity including a prepared tooth arranged into a shape for receiving the temporary prosthesis;
    fabricating a prosthesis model (W) having a shape that is identical to a shape of the temporary prosthesis to be formed on the prepared tooth model (M);
    using an impression material to take an impression (I) of the prepared tooth model (M) having the prosthesis model (W) mounted thereon;
    applying a layer of dental composite resin material (C) to a portion that is to become a crown within the impression (I) that has been removed from the prepared tooth model (M) and polymerizing the dental composite resin material (C);
    putting a powder-liquid mixture of a powder-liquid type room temperature polymerization resin (R) into the impression (I);
    removing the prosthesis model (W) from the prepared tooth model (M); and
    refitting the prepared tooth model (M) to the impression (I) and curing the room temperature polymerization resin (R).

2. A method for producing a temporary prosthesis, the method comprising the steps of:
    fabricating a model (M') replicating an oral cavity including a tooth that is to receive the temporary prosthesis based on an impression (I) of the oral cavity including the tooth;
    fabricating a prepared tooth model (M) replicating an oral cavity including a prepared tooth arranged into a shape for receiving the temporary prosthesis;
    applying a layer of dental composite resin material (C) to a portion that is to become a crown within the impression (I) that has been removed from the prepared tooth model (M) and polymerizing the dental composite resin material (C);
    putting a powder-liquid mixture of a powder-liquid type room temperature polymerization resin (R) into the impression (I);
    fitting the prepared tooth model (M) to the impression (I) and curing the room temperature polymerization resin (R).

3. The method for producing a temporary prosthesis as claimed in claim 1, wherein
    the dental composite resin material (C) includes a (meth)acrylate compound, a polymerization initiator, and a filler; and
    a ratio of the filler is 45 wt % to 80 wt % of the dental composite resin material (C).

4. The method for producing a temporary prosthesis as claimed in claim 1, wherein
    the powder-liquid mixture of the room temperature polymerization resin (R) includes a liquid component containing a (meth)acrylate compound and a room temperature polymerization initiator, and a powder component containing a poly((meth)acrylate) powder and a room temperature polymerization initiator; and
    a ratio of a filler mixed into the powder component is less than or equal to 10 wt %.

* * * * *